United States Patent [19]

Huerta

[11] Patent Number: 5,311,864
[45] Date of Patent: May 17, 1994

[54] TRACHEAS EVACUATION AND TRANSMITTAL TUBE

[76] Inventor: Christine M. Huerta, 2548 Indian Ave., Belleair, Fla. 34640

[21] Appl. No.: 989,390

[22] Filed: Dec. 11, 1992

[51] Int. Cl.[5] ............................................. A61M 16/00
[52] U.S. Cl. .......................... 128/207.15; 128/207.17
[58] Field of Search ................... 128/200.26, 207.14, 128/207.15, 207.17; 604/97, 98, 103

[56] References Cited

U.S. PATENT DOCUMENTS

| | | | |
|---|---|---|---|
| 3,544,668 | 12/1970 | Dereniuk | 604/103 |
| 3,734,100 | 5/1973 | Walker et al. | 604/103 |
| 4,231,365 | 11/1980 | Scarberry | 128/207.15 |
| 4,305,392 | 12/1981 | Chester | 128/207.15 |
| 4,327,721 | 5/1982 | Goldin et al. | 128/207.15 |
| 4,334,534 | 6/1982 | Ozaki | 128/207.15 |
| 4,584,998 | 4/1986 | McGrail | 128/207.15 |
| 4,607,635 | 8/1986 | Heyden | 128/207.15 |
| 4,693,243 | 9/1987 | Buras | 128/207.15 |
| 4,762,125 | 8/1988 | Leiman et al. | 128/207.15 |
| 4,955,375 | 9/1990 | Martinez | 128/207.15 |
| 4,976,261 | 12/1990 | Gluck et al. | 128/207.14 |
| 5,065,755 | 11/1991 | Klaffa | 128/207.15 |
| 5,065,757 | 11/1991 | Dragisic et al. | 128/207.15 |
| 5,067,497 | 11/1991 | Greear et al. | 128/207.15 |
| 5,143,062 | 9/1992 | Peckham | 128/207.15 |
| 5,146,916 | 9/1992 | Catalani | 128/207.15 |

Primary Examiner—Edgar S. Burr
Assistant Examiner—Aaron J. Lewis
Attorney, Agent, or Firm—Charles E. Lykes, Jr.

[57] ABSTRACT

The invention teaches a means and apparatus which enables the safe and effective evacuation of fluids or dispensing of medication to a patient undergoing breathing assistance by means of either an endotracheal breathing tube or a tube inserted through a tracheal incision, either tube being equipped with a balloon cuff. It comprises an evacuation sheath, balloon cuff lumen, and optional lumen with a reinforced balloon cuff upper end to promote uninterrupted breathing assistance and balloon cuff operations. A plate is taught which makes these functions available to patients who have required tracheal incisions in order to insert the breathing tube.

10 Claims, 4 Drawing Sheets

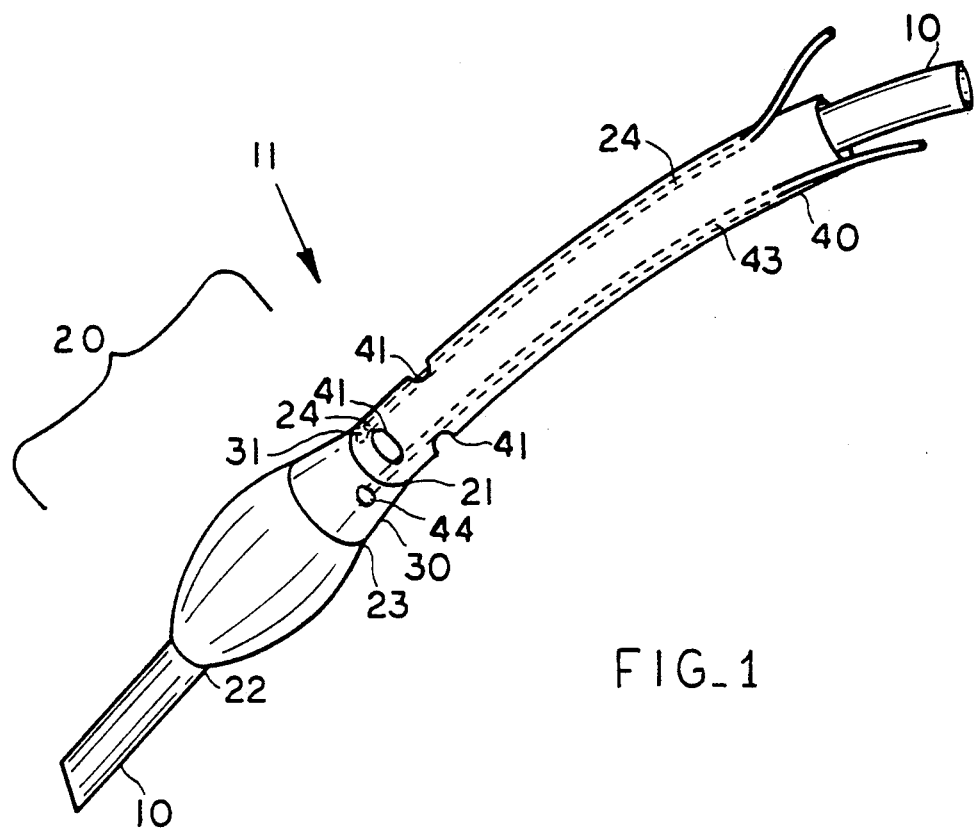
FIG_1

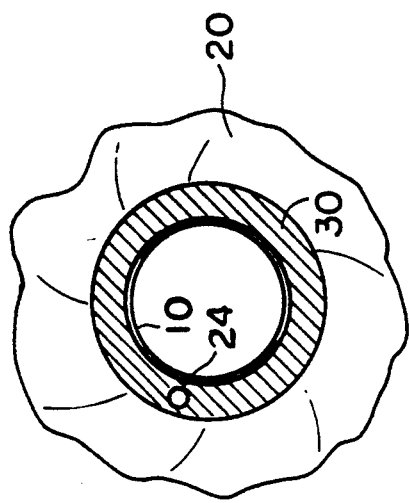
FIG_2B
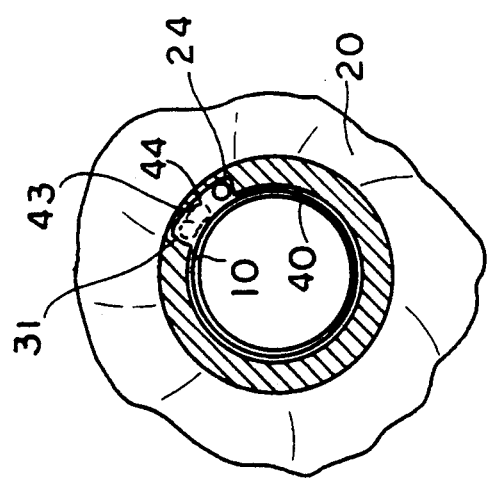
FIG_2A

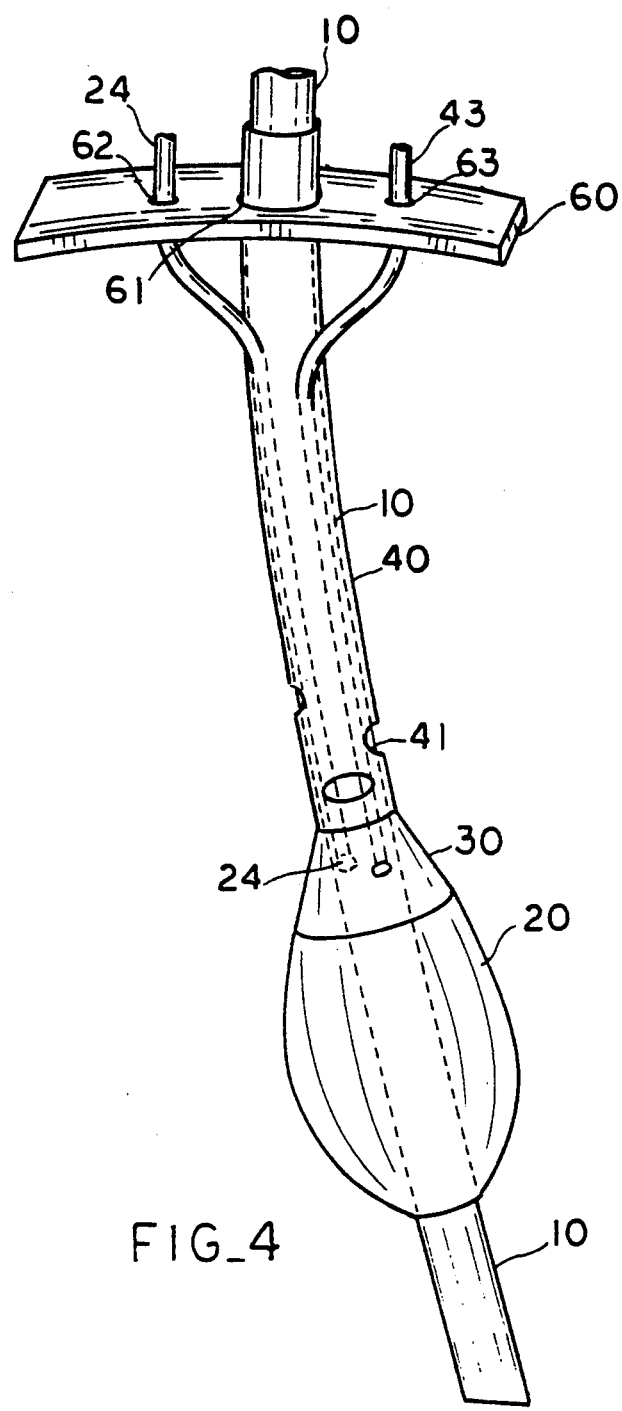
FIG_4

TRACHEAS EVACUATION AND TRANSMITTAL TUBE

The invention relates to medical devices, particularly those having to do with breathing assistance tracheal tubes. Reference is made to United States Patent Office Disclosure Document number 309,911 filed by the inventor on May 18, 1992.

When a patient is under anaesthesia, undergoing critical care treatment, or requires extraordinary breathing assistance, a breathing tube may be inserted through the tracheal region or from mouth to lungs in order to artificially ventilate a patient or to create a patent airway. Sometimes such a tube is inserted through an incision in the trachea and then in to the lungs. Such a tube facilitates the artificial insertion of air into the patient's lungs.

The sickened condition of the patient, the existence of foreign material in the tracheas, and the continual exposure to the ambient air brought about by a permanent opening of the mouth or other region to permit the passage of the tube result in an increased exposure to germs and bacteria as well as the secretion of fluids in the tracheal region. It is critical to devise a means of preventing either the fluid or the bacteria from passing into the lungs.

This is typically done by adapting the air tube with a balloon device at some point along its length. The balloon device can be pumped full of air to block the passage of any fluid or gas other than the air passing through the tube. A balloon cuff is typically used to prevent undesired backflow of air from the patient's lung cavity and ensure proper ventilation of the patient. This balloon cuff provides a collection area for the undesired fluid or bacteria.

A variety of prior art devices have taught means of evacuating such fluids and secretions from the tracheal region. Such prior art devices commonly comprise as common elements of an inflatable or balloon cuff to block the passage of and collect the undesired fluids and an evacuation path through which the undesired may be vacuumed out of the tracheal region.

U.S. Pat. No. 4,762,125, issued to Leiman, et al, on Aug. 9, 1988, describes an apparatus for evacuating such fluids from a tracheal tube. An evacuation tube with a balloon cuff and closed end can be inserted within an endotracheal tube. Fluids or gas are channeled into the system through openings in the evacuation system upward from the balloon cuff and can be suctioned from the tracheal tube. The Leiman device blocks passage of air or oxygen through the endotracheal tube. It does not provide for evacuation of such fluids from outside the endotracheal tube.

U.S. Pat. No 3,087,493, issued to Schossow on Apr. 30, 1963, teaches a balloon cuff apparatus with separate air insertion and evacuation lumens. The evacuation chamber of Schossow is on the distal side of the balloon cuff apparatus. No means is provided for preventing the passage of such undesired fluids or gases past the balloon cuff.

U.S. Pat. No. 4,305,392, issued to Chester on Dec. 15, 1981, teaches an endotracheal tube with balloon cuff and means for evacuating undesired fluids from the proximal (or upward) side of the balloon cuff. The evacuation chamber of Chester teaches a rigid bulged cuff about the endotracheal tube. The bulged cuff is adapted with four suction ports adjacent to the outer wall of the endotracheal tube at the proximal side of the bulged cuff. Undesired fluids flowing down the outer wall of the endotracheal tube might flow into one of the suction ports (four are recommended in order to protect structural integrity) to be sucked into the chamber and out through a lumen within the endotracheal tube wall. The diameter of the bulb has a direct relationship with the size of the endotracheal tube. Upon oral insertion the bulb can obstruct direct visualization of the vocal cords which must be passed through for proper placement.

In particular, U.S. Pat. No. 4,840,173, issued to Porter III on Jun. 20, 1989, has sought to improve the state of the art in such endotracheal evacuation apparatus. Porter III teaches an evacuation tube which runs alongside the ventilation tube and terminates with an opening immediately adjacent to the balloon cuff. The balloon cuff is adapted with a more rigid material at its proximal side to prevent deflation by the suction of the tube or interference with the suction by any of the balloon surface blocking the opening. Other suction openings are provided just above (or proximal) from this cuff-adjacent opening. It should be noted that all of the openings are along the suction side of the ventilation tube and that only those fluids in that region can easily be evacuated. The single opening in the evacuation tube taught by Porter III exposes the balloon cuff to the full evacuation pressure at that point. It also makes the evacuation function vulnerable to a blockage of the port.

It would be useful to provide such an endotracheal suction device which could more efficiently pool undesired fluids from points all around the ventilation tube. It would also be useful to provide a suction means with no possibility of interference with or by the balloon cuff.

It should also be noted that some breathing assistance tubes are inserted directly into the tracheal region through an incision made below the epiglottis. It would be desirable to provide a means of providing an apparatus to safely accomplish the ventilation and evacuation functions which could be quickly inserted through a tracheal incision and further facilitate sealing of the tracheal incision.

SUMMARY OF THE INVENTION

The inventor has solved the problems remaining from the prior art with an apparatus which facilitates the gathering of undesired fluids from all around the ventilation tube as well as points all around the tracheal region above the balloon cuff. The present invention additionally facilitates the safe and efficient evacuation of those fluids with no possibility of interference of or by the operation of the balloon cuff. An alternative embodiment of the apparatus includes a tracheal plate to seal a tracheal incision and to facilitate fluid communication between the various suction and ventilation sources and their respective evacuation and ventilation areas.

The invention generally comprises a ventilation tube with surrounding balloon cuff. A concentric evacuation tube surrounds the ventilation tube for virtually its entire proximal length or at least from immediately above the cuff up until leaving the patient's tracheal region, either above the epiglottis or through a tracheal incision. A rigid collar member separates the balloon cuff from an evacuation region within the evacuation tube and surrounding the ventilation tube. The rigid collar member also serves to assist the collection of fluids at the distal evacuation tube end.

A lumen for inflating and deflating the balloon cuff may be passed through either the evacuation tube or ventilation tube into the balloon cuff without ever opening in the evacuation tube area. A lumen for evacuating the evacuation area is also passed through the evacuation tube and terminates with an open end along the rigid collar member.

For tracheal incision insertion, and evacuation lumens are passed through a plate which rests snugly against and seals the tracheal incision. The length of the concentric evacuation tube must be the same size or longer than the distance from the cuff to the tracheal incision.

The concentric evacuation tube may be adapted with a series of ports about its exterior surface just proximal from the cuff. Undesired fluids will be efficiently pooled and isolated at the rigid collar member from all around the ventilation tube. Additional fluids may be collected from the ports in the evacuation tubes. All of these fluids can be safely and efficiently evacuated through the evacuation lumen.

It is, then an object of the present invention to provide a more efficient and safe endotracheal or tracheostomy ventilation and evacuation apparatus.

It is a further object of the present invention to provide such an apparatus with the capability of isolating undesired fluids from all around the ventilation tube for efficient evacuation.

It is a further object of the present invention to provide such an apparatus with no possibility of interference between the balloon cuff and evacuation functions.

It is a further object of the present invention to provide means for safe and efficient use of such ventilation and evacuation device in conjunction with a tracheal incision.

It is further object of the present invention to provide such functions and also provide a means for introducing fluids to the trachea through the evacuation tube chamber of a endotracheal or tracheostomy device.

Other features and advantages of the present invention will be apparent from the following description in which the preferred embodiments have been set forth in conjunction with the accompanying drawings.

BRIEF DESCRIPTION OF THE DRAWINGS

In describing the preferred embodiments of the invention reference will be made to the series of figures and drawings briefly described below.

FIG. 1 depicts the overall apparatus from the side permitting viewing of the balloon cuff, ventilation and evacuation tubes, and evacuation and cuff lumens.

FIG. 2A, and 2B depict cross-section views of the apparatus at the proximal and distal sides of the balloon cuff respectively permitting viewing of the rigid collar member, balloon cuff, and cross sectional views of ventilation and evacuation tubes and evacuation and cuff lumens.

FIG. 4 depicts the basic apparatus adapted with a plate for use of the basic apparatus within and through a tracheal incision.

DETAILED DESCRIPTION OF THE PREFERRED AND ALTERNATE EMBODIMENTS

Figure 3:
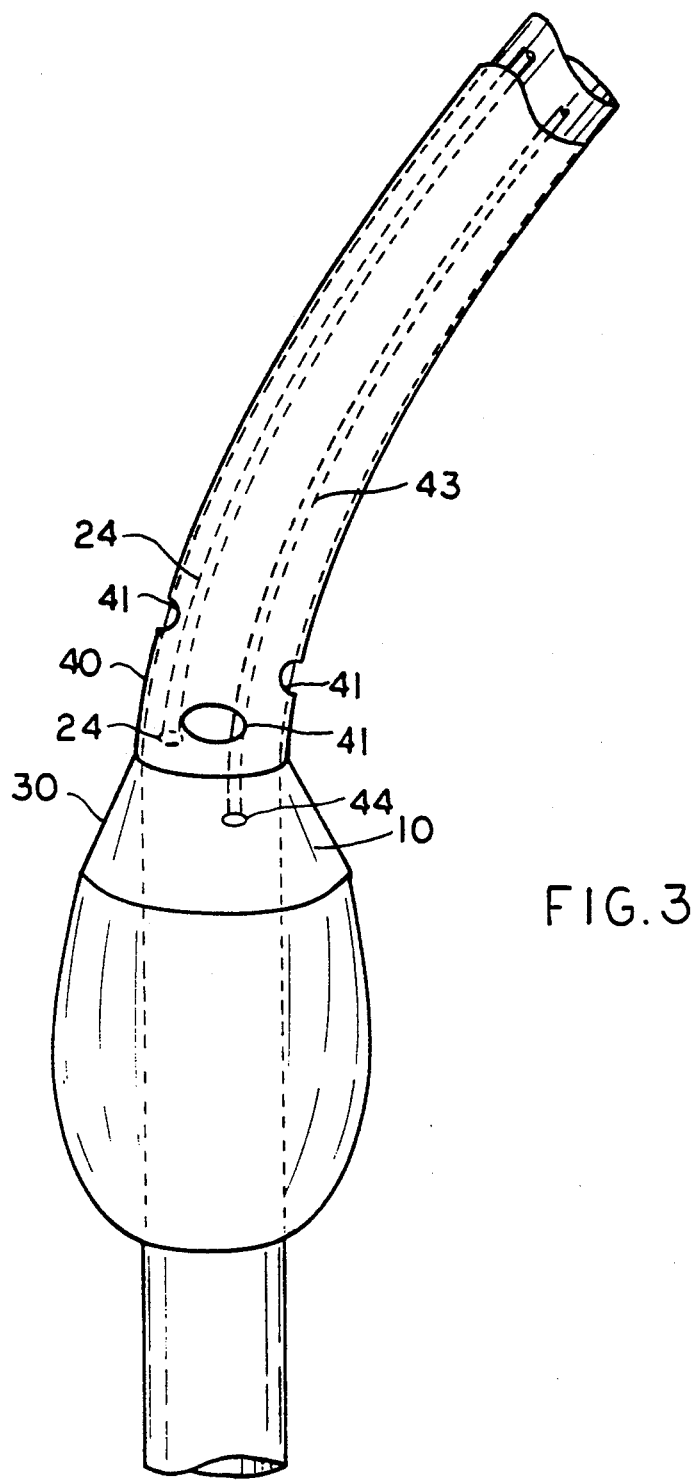
FIG. 3 is a close up oblique depiction of the apparatus in the region of the proximal side of the balloon cuff depicting the relationship between balloon cuff, rigid collar member, evacuation tube, and ventilation tube and operation of the evacuation and cuff lumens.

Making reference first to FIG. 1, the major components of the apparatus are identified. A ventilation tube (10) runs throughout a length sufficient to pass through a patient's mouth and into the lung opening (neither of which are depicted). A balloon cuff (20) is placed about the ventilation tube (10) at a position (11) so that it will be between the patient's epiglottis (not depicted) and lung opening (not depicted). The membrane (24) of the balloon cuff (20) is radially connected to the ventilation tube (10) at its distal end (22). At its proximal end (23), the balloon cuff membrane (21) is radially connected to a relatively more rigid collar member (30) which comprises the proximal end of the balloon cuff and is itself in full radial connection with and radially protrudes from the ventilation tube (10). Ideally, the rigid collar member (30) tapers in thickness from its point of connection about the ventilation tube into the balloon cuff membrane (21). This rigid collar member (30) protects the balloon cuff membrane (21) from being damaged by suction through the evacuation tube.

Concentrically about the ventilation tube (10) and extending proximally from the rigid collar member (30) is depicted an evacuation sheath (40). The evacuation sheath (40) must be of a width sufficient to ensure the pooling of fluids in the region of the rigid collar member (30) about the ventilation tube (10). The evacuation sheath (40) may also be adapted with a series of ports (41) at points about its circumference and near the rigid collar member (30). These ports (41) would be of adequate dimension to permit fluids to enter the evacuation sheath (40). These fluids may then flow down to the rigid collar member (30). The evacuation sheath (40) must be of an adequate length to pass from the rigid collar member (30) back up through the tracheal region and then out of the patient through either the patient's mouth or an incision in the tracheal region (areas are not depicted).

The evacuation sheath (40), at a point outside the patient's body, is gathered into a lumen (not depicted in FIG. 1) which permits fluid pressure communication throughout the evacuation sheath (40). One or more additional evacuation lumens (43) may, but need not, similarly be used to run along the ventilation tube (10) in order to provide evacuation at specific areas along the ventilation tube (10). Such a lumen (43) could also be used (with reverse pressure) to deliver medication to the points. When used, such an evacuation lumen (43) must be positioned in a manner which does not interrupt the fluid pressure from within the evacuation sheath (40) to a point outside the patient's body.

From outside the patient and then through the space (42) within the evacuation sheath (40), but outside the ventilation tube (10), and to the rigid collar member (30) may run an evacuation lumen (43) and a balloon cuff lumen (24). The evacuation lumen (43), if used, distally terminates with an opening (44) which may (but need not) be fastened along the proximal side (31) of the rigid collar member (30). In this manner the evacuation lumen (43) is able to make fluid pressure communication with fluids flowing down to the sheath. The proximal end (not depicted) of the evacuation lumen (43) may be in communication with a vacuum source (not depicted).

The balloon cuff lumen (24) distally terminates into a port (32) in the rigid collar member (30) which opens into the balloon cuff interior (25). The proximal end (not depicted) of the balloon cuff lumen (24) may be in communication with alternating sources of pressure and vacuum to facilitate inflating and deflating the space between the balloon cuff membrane (21) and the ventilation tube (10). As their integral construction results in no contact or other friction between the balloon cuff (20) and any moving part of the rigid collar member (30), there is little or no chance of puncture.

Some comment should be made about the proximal end of the ventilation tube (10). In the case of an endotracheal device, the distal end of the ventilation tube (10) is long enough to pass through the mouth of the patient with the balloon cuff (20) positioned between the epiglottis and lung. This configuration is depicted in FIG. 1. A pumping and ventilation means (not depicted) at this proximal end may be used to ventilate the patient's lungs. Additionally, the balloon cuff (24) and evacuation lumen (43) are each of adequate length to be passed out through the patient's mouth from these positions. Pumping and pressure devices connected thereto can be used to perform the functions of balloon inflation and deflation and suction of the undesired fluids.

Making reference now to FIG. 4, an alternative embodiment of the present invention is described. Such alternative embodiment incorporates the art taught in the preferred embodiment and is in keeping within the spirit and scope of the present invention.

There are occasions, however, when it is necessary to perform the breathing augmentation function from an incision through the tracheas. This may be the result of trauma or blockage. This is commonly done by making an incision into the tracheal region through the neck which is large enough to pass the various lumens and tubes. Such incisions are typically made below the larynx. It can be seen that this presents an additional exposure to the risk of infection. Secretions build up on top of the cuff and leak out of the surgical incision onto the patient's chest, creating a medium for infection to the surgical site.

In order to control this risk as well as to facilitate the utility of the breathing assistance components as described above, the inventor has developed a plate (60) which may be used to cover the incision and maintain an appropriate position and spatial relationship between the various tubes and lumens. Such a plate (60) is depicted in FIG. 4. It can be seen that the plate (60) is designed to generally fit the curvature of the neck and to cover the tracheal incision (70).

Whereas present plates are shaped with a curvature below the ventilation tube (presumably in order to nestle with the clavicle wedge) the present plate is seen as a straight band. Eliminating the curvature avoids potential aggravation of the swollen area about the incision.

Through the plate are openings (61, 62, 63) which correspond with the diameters of the ventilation tube (10, 61) and the balloon cuff (24, 62) and evacuation lumens (43, 63). Rather than pass the proximal ends of these channels through the mouth, they can be passed out through the openings (61, 62, 63) in the plate, which also serve to stabilize and help identify and distinguish them from each other.

A primary advantage of this plate (60) is that it may cover tracheal incision. By providing these ports (61, 62, 63) for each of the tubes and lumens required to operate the device, it is unnecessary to make any further entries or incisions in the tracheal region. The incision can be dressed, healed and covered leaving sufficient apparatus available to ventilate, operate the cuff, evacuate the fluids, and, as may be necessary apply medications to the patient's tracheal region. A primary advantage of this plate (60) as adapted with the evacuation lumen port (63) is that it permits the evacuation of the fluids through and away from the plate (10). Formerly these evacuation means could not be applied through a tracheal incision.

The ports (61, 62, 63) may be adapted with caps or covers (64, 65, 66) so that the plate (60) may be left in position but the openings (61, 62, 63) sealed. This would permit rapid and easy reactivation of breathing augmentation as may be necessary with a given patient without making a new tracheal incision.

A secondary benefit of this is in the emotional well being of the patient. Patients who undergo tracheal incisions are typically left with an unsightly wound and dressing in their tracheal region. The wound itself requires frequent attention. With the apparatus adapted with this plate, these drawbacks are avoided. A patient with such an apparatus is more likely to feel comfortable in the presence of family and friends and is less apt to experience discomfort from the need to insert and remove tubes or to have unsecured tubes protruding from the tracheal region.

In order to prevent the inadvertent confusion between ports, the evacuation port and balloon cuff port could be made of different sizes or different means of attachment, or both. This would prevent the patient or attendant from erroneously applying inappropriate pressure or medication, or from otherwise confusing functions. Additionally, while this embodiment has been described with the various lumens and ports terminating at the plate, there is no reason that the lumens and tubes could not be extended through the plate for attachment to any desired source of pressure.

Reference has been made to various sources of vacuum pressure. Such pressure sources are well known in the state of the art and not separately claimed here. It is, however, worth mentioning that, as adapted with the evacuation sheath and optional evacuation lumens, the device as presently taught may be safely operated with either a machine vacuum (at pressures up to −200 cm of water pressure) or manually through a syringe. This makes the device useful either in a hospital or in the course of home care.

Further modification and variation can be made to the disclosed embodiments without departing from the subject and spirit of the invention as defined in the following claims. Such modifications and variations, as included within the scope of these claims, are meant to be considered part of the invention as described.

What is claimed is:

1. A breathing augmentation apparatus for insertion from a point outside a patient's body through the patient's tracheal region in the patient's lung cavity, the apparatus comprising:
a ventilation tube, said ventilation tube being of a flexible material and of diameter adequate to pass sufficient air or oxygen at a pressure safe to a person's lung but small enough to fit through said tracheal region without trauma or damage to the epiglottis or interior throat surfaces and of sufficient length to reach from a point outside said patient's body, through said tracheal region and to the lung cavity opening;
a balloon cuff, said balloon cuff being positioned radially bout said ventilation tube at a point between said patient's epiglottis and lung opening, said balloon cuff further being adapted to alternatively be inflated to permit its expansion radially about said ventilation tube to fill the space between said ventilation tube and throat wall and then be deflated to permit its collapse upon said ventilation tube, said balloon cuff further including a rigid collar member, said rigid collar member extending from the balloon cuff, radially surrounding said ventilation tube and extending a distance sufficient to isolate said balloon cuff from suction applied from the surface of said ventilation tube through the ports of a fluid collar and hold said balloon cuff in place and to permit the insertion of a fluid pressure lumen for inflating and deflating said balloon cuff from a pressure source outside the patient's body; and a fluid collection collar, said collar further comprising a concentric evacuation sheath about said ventilation tube and extending from said rigid collar member proximally and about said ventilation tube to a pressure source outside the patient's body, said fluid collection collar being further provided with at least two ports about its circumference nearer said rigid collar member.

2. The invention described in claim 1 in which said rigid collar member is made of a semi-rigid material which is tapered from its point of connection about said ventilation tube into said balloon cuff membrane.

3. The invention described in claim 1 in which said balloon cuff lumen is positioned along the ventilation tube and within said fluid collection collar from a point within said balloon cuff rigid collar member, through said rigid collar member, and outside the patient's body.

4. The invention described in claims 1, 2 or 3 in which one or more evacuation lumens are placed within said evacuation sheath from a point near the proximal side of said balloon cuff in a means to permit common fluid pressure communication between said evacuation lumens and said evacuation pressure.

5. The invention described in claim 4 in which said rigid collar member is made of a semi-rigid material which is tapered from its point of connection about said ventilation tube into said balloon cuff member.

6. A breathing augmentation apparatus for insertion from a point outside a patient's body through the patient's tracheal region to the patient's lung cavity, the apparatus comprising:

a ventilation tube, said ventilation tube being of a flexible material and of diameter adequate to pass sufficient air or oxygen at a pressure safe to a person's lung but small enough to fit through said tracheal region without trauma or damage to the epiglottis or interior throat surfaces and of sufficient length to reach from a point outside said patient's body, through said tracheal region and to the lung cavity opening;

a balloon cuff, said balloon cuff being positioned radially about said ventilation tube at a point between said patient's epiglottis and lung opening, said balloon cuff further being adapted to alternatively be inflated to permit its expansion radially about said ventilation tube to fill the space between said ventilation tube and throat wall and then be deflated to permit its collapse upon said ventilation tube, said balloon cuff further including a rigid collar member, said rigid collar member extending from said balloon cuff, radially surrounding said ventilation tube and holding said balloon cuff in place and to permit the insertion of a fluid pressure lumen for inflating and deflating said balloon cuff from a pressure source outside the patient's body;

a fluid collection collar, said collar further comprising a concentric evacuation sheath about said ventilation tube and extending from said rigid collar member proximally and about said ventilation tube to a pressure source outside the patient's body, said fluid collection collar being further provided with at least two ports about its circumference near said rigid collar member; and a tracheal plate, said tracheal plate being provided with ports for receiving the proximal ends of said evacuation sheath, ventilation tube, and balloon cuff lumens, said tracheal plate being further adapted to cover a tracheal incision.

7. The invention described in claim 6 in which said rigid collar member is made of a semi-rigid material which is tapered from its point of connection about said ventilation tube into said balloon cuff membrane.

8. The invention described in claim 6 in which said balloon cuff lumen is positioned along the ventilation tube and within said fluid collection collar from a point within said balloon cuff rigid collar member, through said rigid collar member, and outside the patient's body.

9. The invention described in claims 6, 7, or 8 in which one or more evacuation lumens are placed within said evacuation sheath from a point near the proximal side of said balloon cuff in a means to permit common fluid pressure communication between said evacuation lumens and said evacuation pressure.

10. The invention described in claims 6, 7, or 8 in which one or more evacuation lumens are placed within said evacuation sheath from a point near the proximal end of said balloon cuff in a means to permit common fluid pressure communication among each other but separate from that of said evacuation sheath.

* * * * *